United States Patent
Klausman et al.

(10) Patent No.: US 11,759,246 B2
(45) Date of Patent: Sep. 19, 2023

(54) STYLET SCREW DRIVER

(71) Applicant: Astura Medical Inc., Irving, TX (US)

(72) Inventors: Keith Klausman, Irving, TX (US);
Thomas Purcell, Irving, TX (US);
Anthony Valkoun, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 17/883,511

(22) Filed: Aug. 8, 2022

(65) Prior Publication Data
US 2022/0378488 A1 Dec. 1, 2022

Related U.S. Application Data

(63) Continuation of application No. 16/581,711, filed on Sep. 24, 2019, now abandoned.

(60) Provisional application No. 62/735,820, filed on Sep. 24, 2018.

(51) Int. Cl.
*A61B 17/88* (2006.01)
*A61B 17/70* (2006.01)
*A61B 17/86* (2006.01)

(52) U.S. Cl.
CPC ...... *A61B 17/8875* (2013.01); *A61B 17/7074* (2013.01); *A61B 17/7082* (2013.01); *A61B 17/7083* (2013.01); *A61B 17/864* (2013.01); *A61B 17/8819* (2013.01); *A61B 17/8897* (2013.01)

(58) Field of Classification Search
CPC ............ A61B 17/1604; A61B 17/8875; A61B 17/8888; A61B 17/8897; A61B 17/8886; A61B 17/8819; A61B 17/70; A61B 17/7032; A61B 17/7074; A61B 17/7082; A61B 17/864; A61B 17/86; A61B 17/7083; A61B 17/7084; A61B 2017/564
USPC ................................ 606/104, 304, 265, 279
See application file for complete search history.

(56) References Cited

U.S. PATENT DOCUMENTS

| | | | |
|---|---|---|---|
| 7,207,995 B1 * | 4/2007 | Vandewalle | A61B 17/8875 606/104 |
| 9,289,249 B2 * | 3/2016 | Ramsay | A61B 17/7082 |
| 2013/0310842 A1 * | 11/2013 | Winkler | A61B 17/8875 606/104 |
| 2014/0094822 A1 * | 4/2014 | Baynham | A61B 17/7083 606/103 |
| 2014/0276892 A1 * | 9/2014 | Pakzaban | A61B 17/8875 606/104 |
| 2016/0030100 A1 * | 2/2016 | Divincenzo | A61B 17/8875 606/104 |
| 2018/0368893 A1 * | 12/2018 | DiVincenzo | A61B 17/1604 |

* cited by examiner

*Primary Examiner* — Marcela I. Shirsat
(74) *Attorney, Agent, or Firm* — Michael R Shevlin

(57) ABSTRACT

A stylet screw driver assembly having a screw driver/ratcheting handle assembly which houses a stylet, pre-assembled to a set length based on the screw length in use, fixed in place by a spring loaded button mechanism located on the proximal end of the ratcheting handle. The spring loaded button mates with the stylet assembly, providing various stylet protrusion lengths.

17 Claims, 2 Drawing Sheets

STYLET SCREW DRIVER

CROSS-REFERENCE TO RELATED APPLICATIONS

The present application is a continuation application of U.S. patent application Ser. No. 16/581,711, filed Sep. 24, 2019, which claims priority to U.S. Provisional Application No. 62/735,820 filed Sep. 24, 2018, which is incorporated herein by reference.

FIELD

The present invention relates generally to the field of surgery, and more specifically, to a stylet screw driver for use in spinal fusion surgery.

BACKGROUND

Certain spinal conditions, including a fracture of a vertebra and a herniated disc, indicate treatment by spinal immobilization. Several methods of spinal joint immobilization are known, including surgical fusion and the attachment of pins and bone plates to the affected vertebras with screws.

The standard process leading up to screw insertion involves several steps that are time-consuming and cumbersome, especially when a large number of screws are to be inserted. Each step requires fluoroscopic imaging which increases the patient's exposure to radiation potentially causing dangerous complications and or negative long-term health effects.

Thus, there is a need for an improved stylet screw driver that solves the problems listed above.

SUMMARY

The present invention is directed to a screw driver/ratcheting handle assembly which houses a stylet, pre-assembled to a set length based on the screw length in use, fixed in place by a spring loaded button mechanism located on the proximal end of the ratcheting handle. The spring loaded button mates with the stylet assembly, providing various stylet protrusion lengths.

DETAILED DESCRIPTION

The present invention is a stylet screw driver which houses a stylet capable of translating via a rotatable handle. The stylet screw driver may include a screw driver/ratcheting handle assembly which houses a stylet, pre-assembled to a set length based on the screw length in use, fixed in place by a spring loaded button mechanism located on the proximal end of the ratcheting handle. The spring loaded button mates with the stylet assembly, providing various stylet protrusion lengths.

Figure 1:
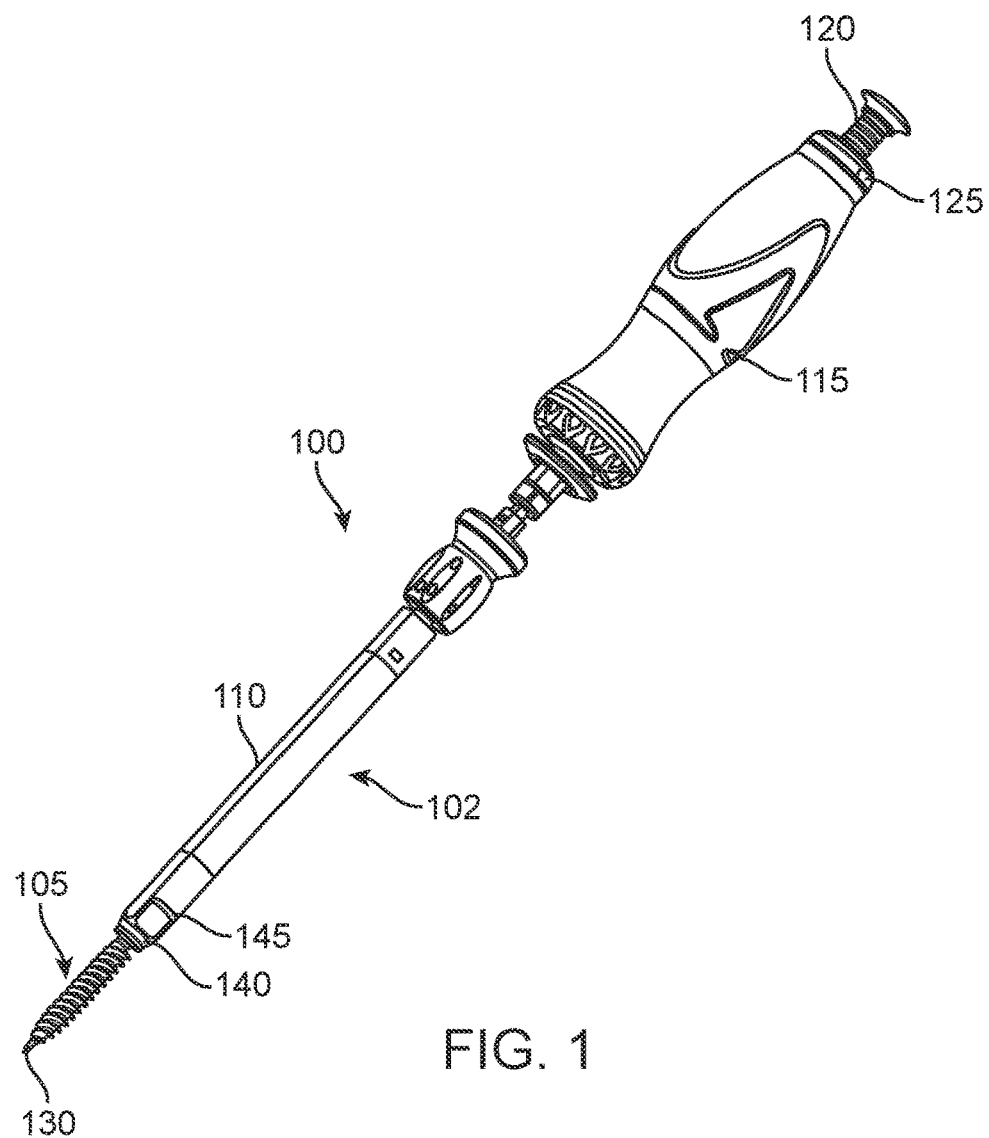
FIG. 1 is a perspective view showing a one embodiment of a stylet screw driver.
Figure 2:
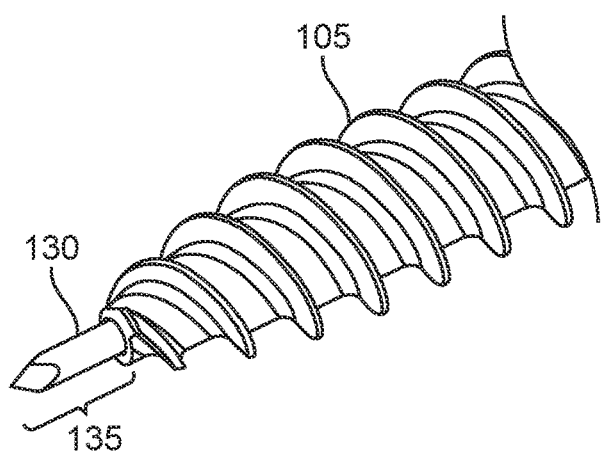
FIG. 2 is a perspective view showing a stylet extending from the tip of a pedicle screw.
Figure 3:
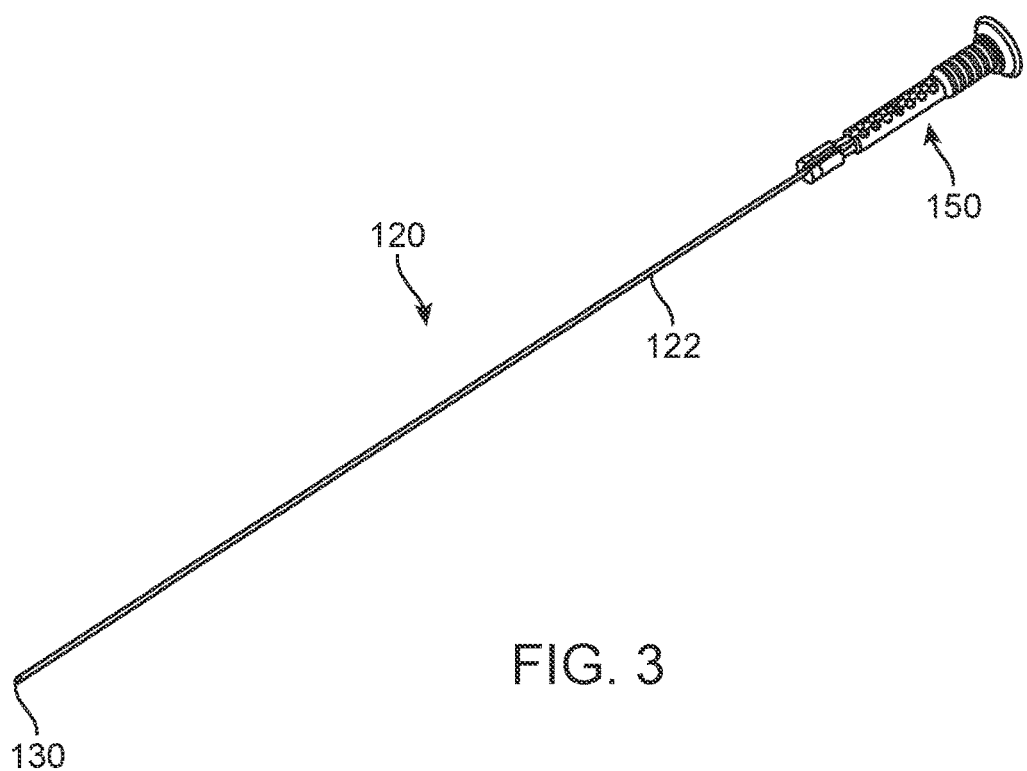
FIG. 3 is a perspective view showing a one embodiment of a stylet assembly.

FIG. 1 shows one embodiment of a stylet screw driver assembly 100 designed to deliver pedicle screws 105 into bone. The stylet screw driver assembly 100 includes a stylet screw driver 102 having a body 110, a screw driver/ratcheting handle assembly 115, and a stylet assembly 120. The body 110 and handle 115 includes a central axial lumen in which the stylet assembly 120 is positioned. The stylet assembly 120 may be pre-assembled to a set length A based on the selected screw length so that a distal end or tip 130 extends distally from the pedicle screw 105. The stylet assembly 120 may be fixed in place within the body 110 and handle 115 by a spring loaded button mechanism 125 located on a proximal end of the handle.

The pedicle screw 105 may be part of a pedicle screw fixation system (PSFS) used for a variety of conditions that affect the spine. The pedicle screw may be a top loading screw having a U-shaped tulip 140 on a proximal end designed to hold rods, crosslinks, and rod connectors of the fixation system. The interior of the U-shaped tulip may be threaded.

The distal end of the body 110 may include a threaded engagement feature 145 configured to engage the threads in the tulip 140. The engagement feature 145 may further include a drive feature to engage a socket on the proximal end of the screw head to drive the pedicle screw 105 into the bone.

Setting Stylet Assembly Length

The stylet assembly 120 includes a stylet 122 and screw length adjustment section 150 configured to set the stylet length. The stylet assembly 120 length is selected based on the screw length, so that the distal end or tip 130 extends a desired distance 135 distally from the pedicle screw 105. The stylet assembly 120 may then be pre-assembled to the set length based on the screw length in use.

Figure 4:
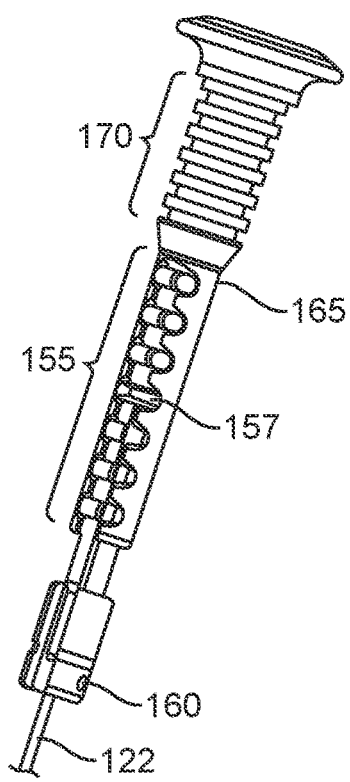
FIG. 4 is a perspective view showing the proximal end of the stylet assembly of FIG. 3.

FIG. 4 shows a plurality of slots 155 spaced apart at set distances to adjust the stylet assembly 120 to the desired distance. A stylet stop 157 is configured to be positioned in the slot 155 and engages the stylet 122 to stop at the selected length when it is inserted into the adjustment section 150. The stylet 122 is then locked in place with a locking mechanism 160

The slots 155 may include labels or features 165 proximate each slot to assist in selecting the appropriate slot for the desired length. For example, the slots 155 may be labeled from 30-60 mm separated in 5 mm increments (30 mm at the top to 60 mm at the bottom). When a screw length is selected, such as a 45 mm screw, the stylet stop 157 is placed in the slot labeled 45 mm is used to fix the length of the stylet assembly 120. The 45 mm screw 105 is then positioned on the distal end 145 and the stylet assembly 120 is pre-assembled with desired length of stylet 135 extending from the distal end.

Adjusting Stylet Protrusion Lengths

The stylet assembly 120 may be fixed in place within the body 110 and handle 115 by a spring loaded button mechanism 125 located on a proximal end of the handle. 115. It may be desirable to make further adjustments of the stylet tip protrusion length 135 once the stylet screw driver assembly 100 is assembled.

Figure 5:
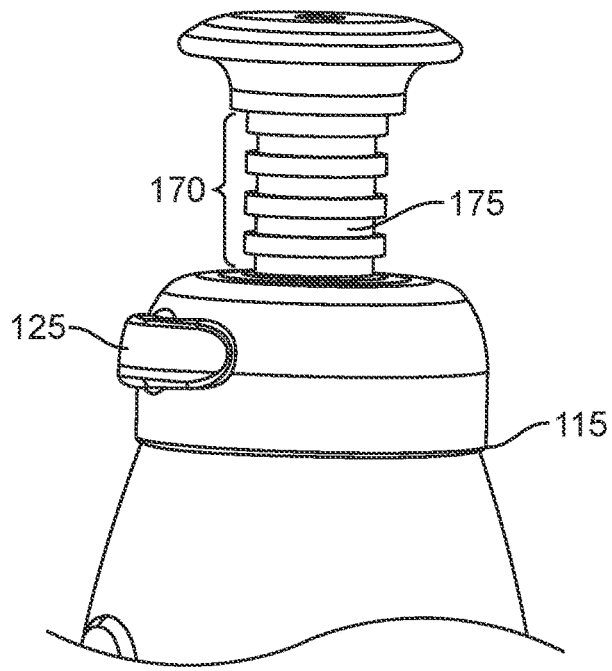
FIG. 5 is a view showing the proximal ends of the stylet assembly and stylet screw driver handle with a spring loaded button mechanism.

FIGS. 4 and 5 show the proximal portion of the stylet assembly 120 having a plurality of tip adjustment slots 170 spaced apart at set distances configured to engage the spring loaded button mechanism 125 on the proximal end of the handle. 115. By depressing the spring loaded button 125, the stylet assembly 120 within the modular ratcheting handle is disengaged and the stylet assembly 120 may be moved to a new screw tip protrusion length 135. The spring loaded button 125 is then released, locking stylet assembly 120.

When the stylet assembly 120 is positioned within the handle 110, the slots or groove 170 are configured to engage the spring loaded button mechanism 125 to lock the stylet assembly 120 in the desired position. Pushing the spring loaded button mechanism 125 disengages the stylet assembly 120, which then can be moved axially relative to the handle 110 to a new slot 170 location. The spring loaded button mechanism 125 is then released and locks the stylet assembly 120 in the new position. The ability to adjust the length of the stylet assembly 120 provides various tip protrusion lengths which aid in guidance.

The tip adjustment slots 170 may be include labels or features 175 in each slot to assist in selecting the appropriate slot for extending the desired length. For example, the slots may be positioned with 3 mm spacing so that the distal tip 130 may be extended further distally in 3 mm increments.

Using the Stylet Screw Driver Assembly

The stylet screw driver 100 may be used with a minimally invasive surgical (MIS) technique. Prior to use, the user determines the screw length desired for the procedure and attaches the desired pedicle screw to the distal end. Then the length of the stylet assembly 120 is adjusted for the selected screw length by moving the stylet 122 to the appropriate slot 155 of the adjustment section 150, then locking the length using the locking mechanism 160. The stylet tip 130 extends distally from the pedicle screw the appropriate length 135. The stylet screw driver 100 is now pre-assembled with the correct stylet tip exposure for the selected screw length.

The MIS process starts by opening the skin to access the bone to which the pedicle screw will be attached. The stylet screw driver assembly 100 is inserted through the opening and the stylet tip 130 is positioned proximate the bone at the desired location. The stylet tip 130 is then inserted into the bone by impacting or other known means.

In some embodiments, it may be desirable to adjust the exposed stylet tip 130 for deeper insertion into the bone. This may be done by pushing the spring loaded button mechanism 125 to release the stylet assembly 120, and extending the stylet assembly 120 axially relative to the handle to extend the stylet tip 130 further distally. The extension distance may be selected using the labels or features 175 on the tip adjustment slots 170. Once the stylet tip 130 is at the new length 135, release the loaded button mechanism 125 to lock the stylet assembly 120 in the desired tip adjustment slot 170.

Once the stylet tip 130 is advanced to the desired length or depth in the bone, the handle can be rotated to insert the pedicle screw into the bone. The stylet screw driver 102 is disengaged from the screw 105 and removed, leaving the pedicle screw 105 in place.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A stylet screw driver assembly comprising:
    a body having a distal end configured to hold a spinal screw;
    a handle portion coupled to the body, the body and handle portion having a lumen therethrough; and
    a stylet assembly configured for insertion in the lumen, the stylet assembly is pre-assembled to a set stylet assembly length, the stylet assembly includes:
        a stylet portion with a distal end or tip;
        a screw length adjustment section slidingly coupled with the stylet portion to the set stylet assembly length;
        a stylet stop configured to engage the stylet portion to stop the distal tip at the set stylet assembly length; and
        a locking mechanism configured to lock the stylet portion at the set stylet assembly length;
    wherein the handle portion includes a stylet tip length adjustment mechanism, and the stylet assembly includes a tip length adjustment portion configured to engage the stylet tip length adjustment mechanism to make adjustments to a different tip protrusion length if needed.

2. The stylet screw driver assembly of claim 1, wherein set stylet assembly length is selected based on the spinal screw length so that a tip protrusion length of the distal end or tip extends a desired distance distally from the spinal screw.

3. The stylet screw driver assembly of claim 1, wherein the screw length adjustment section includes a plurality of screw length slots spaced apart at set distances, and the stylet stop is configured to be placed in a screw length slot to fix the stylet assembly length.

4. The stylet screw driver assembly of claim 3, wherein the plurality of screw length slots include screw length labels or features proximate each screw length slot corresponding a different spinal screw length.

5. The stylet screw driver assembly of claim 1, wherein the stylet tip length adjustment mechanism includes a spring loaded button mechanism and the tip length adjustment portion includes a plurality of tip length slots configured to engage the spring loaded button mechanism to lock the pre-assembled stylet assembly.

6. The stylet screw driver assembly of claim 5, wherein the spring loaded button mechanism is configured to disengage with the tip length slot when depressed so that the pre-assembled stylet assembly within the handle portion may be moved to a new tip length slot, the spring loaded button mechanism is configured engages the tip adjustment slots when released and lock the stylet assembly at the new tip length slot.

7. The stylet screw driver assembly of claim 1, wherein the tip length slots include tip length labels or features configured to assist in selecting the appropriate slot for extending the screw tip protrusion length.

8. A stylet screw driver assembly comprising:
    a body having a distal end configured to hold a spinal screw;
    a handle portion coupled to the body, the body and handle portion having a lumen therethrough; and
    a stylet assembly configured for insertion in the lumen, the stylet assembly is pre-assembled to a set stylet assembly length based on a spinal screw length, the stylet assembly includes:
        a stylet portion with a distal end or tip;
        a plurality of screw length slots spaced apart at set distances slidingly coupled with the stylet portion to the set stylet assembly length;

a stylet stop configured to be placed in a screw length slot to stop the distal tip at the set stylet assembly length; and a locking mechanism configured to lock the stylet portion at the set stylet assembly length;

wherein the handle portion includes a spring loaded button mechanism and the stylet assembly includes a plurality of tip length slots configured to engage the spring loaded button mechanism to lock the pre-assembled stylet assembly.

9. The stylet screw driver assembly of claim 8, wherein set stylet assembly length is selected based on the spinal screw length, so that a tip protrusion length of the distal end or tip extends a desired distance distally from the spinal screw.

10. The stylet screw driver assembly of claim 8, wherein the plurality of screw length slots include screw length labels or features proximate each screw length slot corresponding a different spinal screw length.

11. The stylet screw driver assembly of claim 8, wherein the spring loaded button mechanism disengages the tip length slot when depressed and the pre-assembled stylet assembly within the handle portion may be moved to a new tip length slot.

12. The stylet screw driver assembly of claim 8, wherein the tip length slots include tip length labels or features configured to assist in selecting the appropriate slot for extending the screw tip protrusion length.

13. The stylet screw driver assembly of claim 8, wherein the spring loaded button mechanism engages the tip adjustment slots when released and is configured to lock the stylet assembly at the new tip length slot.

14. A stylet screw driver assembly comprising:

a stylet screw driver having a lumen and a distal end configured to couple with a screw, and a stylet slidably positioned within the lumen, the stylet configured to extend distally from the distal end of the stylet screw driver;

a stylet assembly configured to be pre-assembled to a set stylet assembly length based on a spinal screw length, the pre-assembled stylet assembly configured for insertion in the lumen, the stylet assembly includes:

a stylet portion with a distal end or tip;

a plurality of screw length slots spaced apart at set distances slidingly coupled with the stylet portion to the set stylet assembly length;

a stylet stop configured to be placed in a screw length slot to stop the distal tip at the set stylet assembly length; and a locking mechanism configured to lock the stylet portion at the set stylet assembly length;

wherein the stylet screw driver includes a handle portion having a spring loaded button mechanism and the stylet assembly includes a plurality of tip length slots configured to engage the spring loaded button mechanism to lock the pre-assembled stylet assembly.

15. The stylet screw driver assembly of claim 14, wherein the plurality of screw length slots include screw length labels or features proximate each screw length slot corresponding a different spinal screw length.

16. The stylet screw driver assembly of claim 14, wherein the spring loaded button mechanism is configured to disengage with the tip length slot when depressed so that the pre-assembled stylet assembly within the handle portion may be moved to a new tip length slot, the spring loaded button mechanism is configured to engage the tip adjustment slots when released and lock the stylet assembly at the new tip length slot.

17. The stylet screw driver assembly of claim 14, wherein the tip length slots include tip length labels or features configured to assist in selecting the appropriate slot for extending the screw tip protrusion length.

\* \* \* \* \*